United States Patent [19]

Cross et al.

[11] 3,941,881

[45] Mar. 2, 1976

[54] NOVEL 3 OR 5-AMINOPYRAZOLIUM SALTS AND FUNGICIDAL USE THEREOF

[75] Inventors: Barrington Cross, Rocky Hill; Bryant Leonidas Walworth, Pennington, both of N.J.

[73] Assignee: American Cyanamid Company, Stamford, Conn.

[22] Filed: Mar. 14, 1975

[21] Appl. No.: 558,610

[52] U.S. Cl. ............... 424/250; 424/263; 424/273
[51] Int. Cl.² ........................................... A01N 9/22
[58] Field of Search ............... 424/250, 263, 273; 150/280, 27 G, 480

[56] References Cited
UNITED STATES PATENTS

| | | | |
|---|---|---|---|
| 3,341,413 | 9/1967 | Tocus et al. | 424/263 |
| 3,354,167 | 11/1967 | Klosa | 424/263 |
| 3,491,097 | 1/1970 | Koppe et al. | 424/250 |
| 3,544,585 | 12/1970 | Swett et al. | 424/250 |
| 3,655,690 | 4/1972 | Hobbs et al. | 424/250 |
| 3,818,096 | 6/1974 | Sherlock | 424/273 |

OTHER PUBLICATIONS

Chemical Abstracts, Vol. 70: 27848a (1973).

*Primary Examiner*—Donald B. Moyer
*Attorney, Agent, or Firm*—Harry H. Kline

[57] ABSTRACT

There are provided certain novel 1,2-dimethyl pyrazolium compounds having nitrogen containing substituents in the 3 or 5 position, and to both a method for controlling plant pathogenic fungi with said compounds and a method for protecting plants from an attack by fungi by applying to the foliage of plants a fungicidally effective amount of said compound.

6 Claims, No Drawings

NOVEL 3, OR 5-AMINOPYRAZOLIUM SALTS AND FUNGICIDAL USE THEREOF

The present invention relates to novel pyrazolium compounds and methods for preparing the same. More particularly, it relates to compounds having the formula:

(I) 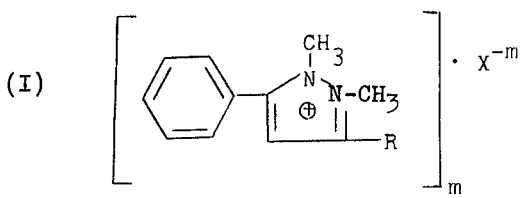

wherein R is 4-pyridyl or a member represented by the formula;

where $R_1$ and $R_2$ each are members selected from the group consisting of hydrogen, alkyl $C_1$-$C_6$, cycloalkyl $C_3$-$C_6$, benzyl, phenyl, 2,3-xylyl and when $R_1$ and $R_2$ are taken together with the nitrogen to which they are attached, they form the moiety:

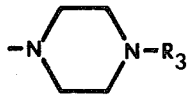

where $R_3$ is hydrogen or methyl; X represents an anion having a charge of from 1 to 3; and m is an integer from 1 to 3.

In general, a plurality of anions in the hereinabove defined compounds can be employed.

Illustrative of the anions which are particularly suitable for use in the present invention may be mentioned, for example, halides, such as chloride, bromide or iodide; acetate, sulfate, hydrogen sulfate, methyl sulfate, benzene sulfonate, $C_1$-$C_4$ alkyl benzene sulfonate, preferably p-toluene sulfonate, nitrate, phosphate, carbonate, and perchlorate.

With regard to pyrazolium salts of the present invention, it is to be understood that certain multivalent anions such as sulfate, phosphate, and the like, may have associated with them a cation in addition to the pyrazolium cation, as for example, a proton or an alkali metal or alkaline earth metal. For simplicity, such anions are portrayed as being unionized, although they probably are in fact further ionized. Typical representations are: $NaSO_4^-$, $KPO_4^{--}$, $MgPO_4^-$, $HSO_4^-$, $NaHPO_4^-$, and the like.

The compounds defined by formula (I) above are unexpectedly capable of controlling plant pathogenic fungi. More specifically, the method of the present invention surprisingly protects plants from an attack by fungi by applying to the foliage thereof a fungicidally effective amount of desired compound.

In general, the pyrazolium compounds defined in the instant specification, can be prepared by reacting a 3-halo-1,2-dimethyl-5-phenylpyrazolium salt with an equimolar amount, or an excess (i.e. 20 to 50 percent molar excess) of an amine of the formula $HNR_1R_2$ wherein $R_1$ and $R_2$ are as defined above, in the presence of a solvent, such as a lower alcohol $C_1$-$C_4$, a lower $C_1$-$C_3$ ketone or acetonitrile at reflux, for a reaction period of from about 1 hour to 24 hours, and preferably from 3 to 8 hours. Thus, in the preparation of 1,2-dimethyl-5-phenyl-3-(4-pyridyl)-pyrazolium iodide, the known 1-phenyl-3-(4-pyridyl)-1,3-propanedione is treated with sym-dimethylhydrazine hydriodide to yield 1,2-dimethyl-5-phenyl-3-(4-pyridyl)pyrazolium iodide directly.

The conversion of water soluble pyrazolium sulfates to water insoluble perchlorates, iodides or tetrafluoroborates is accomplished by the addition of either sodium perchlorate, sodium iodide or sodium tetrafluoroborate to the aqueous pyrazolium methyl sulfate solutions. The thusformed salts precipitate out from the solutions.

The compounds of the present invention, as represented by formula (I) above, and derivatives thereof, are highly effective foliar fungicidal agents. They are particularly effective when applied to the foliage of plants infested with pathogenic fungi at a rate between about 0.56 kg and 11.2 kg per hectare and preferably from 0.56 kg per hectare.

The compounds of the present invention are also effective for protecting living plants from an attack by fungi by applying to the foliage of said plants a compound of present invention at a rate between about 0.56 kg and 11.2 kg per hectare.

For application of the formula (I) pyrazolium compounds to the foliage of plants, the compounds are generally formulated as fungicidal compositions by admixing a fungicidal adjuvant with a fungicidally effective amount of said compounds. Suitable adjuvants include one or more conventional solid or liquid carriers, diluents and formulation aids, particularly surfactants.

The active pyrazolium compounds can be formulated as dusts, dust concentrates, wettable powders or emulsifiable concentrates. However, the emulsifiable concentrates are preferred.

Dusts are readily prepared by grinding together about 1 to 25 percent by weight of the active agent with from about 99 to 75 percent by weight of a solid diluent such as kaolin, attapulgite diatomaceous earth, or the like. Dust concentrates are prepared in similar fashion excepting that about 25 to 95 percent by weight of the active agent is ground with about 75 to 5 percent and weight of the diluent.

Wettable powders are prepared in the same manner as the dust concentrates excepting that about 1 to 5 percent by weight of a dispersing agent such as sodium lignosulfonate, or the sodium salt of condensed naphthaline sulfonic acid is blended with the mixture and about 1 to 5 percent of a surfactant, such as polyoxyethylated vegetable oil or an alkyl phenoxy polyoxyethylene ethanol, is also blended with the formulation. In practice, the powder is mixed with water and applied to the plant foliage as an aqueous spray.

Emulsifiable concentrates are prepared by dissolving from 15 to 70 percent of the compound in 85 percent to 30 percent of a water-miscible solvent, such as water itself on another polar water-miscible solvent, such as 2-methoxy ethanol, methanol, propylene glycol, diethylene glycol, diethylene glycol monoethyl ether, formamide and methylformamide, containing 1 to 5 percent of a surfactant, such as TWEEN 20, a polyoxyethylene sorbitan monolaurate surfactant by Atlas Chemical Industries, or the like. Application of the material is made by adding a predetermined quantity of the emulsifiable concentrate to a spray tank and applying the concentrate as such or in combination with an additional quantity of water or other polar solvent as a liquid spray.

The invention is further illustrated by the examples set forth below. These examples are provided only by way of illustration and are not intended to be limiting the invention.

EXAMPLE 1

Preparation of 1,2-Dimethyl-3-benzylamino-5-phenylpyrazolium Iodide

A mixture of 3-chloro-1,2-dimethyl-5-phenylpyrazolium iodide (6.6 g, 0.02 mole) ethanol (70 ml) and benzylamine (4.6 g, 0.21 mole) is heated at reflux for 7 hours. The mixture is cooled to room temperature and let stand overnight. It is then filtered and the filtrate evaporated to dryness. The residual solid is dissolved in hot water, and the solution treated with aqueous sodium bicarbonate solution, extracted with ether then with chloroform. The chloroform layer is evaporated leaving a residual oil which does not crystallize. The oil is dissolved in cold water and the solution stored four days in a refrigerator. A cream colored solid deposited and is filtered off; m.p. 55°C to 57°C and dried at room temperature in vacuo. 5.3 Grams product (63 percent) is obtained as the monohydrate, m.p. 57°C to 59°C.

Analysis Calculated for $C_{18}H_{20}N_3I.H_2O$: C, 51.07; H, 5.24; N, 9.92. Found: C, 51.20; H, 5.07; N, 9.94.

EXAMPLE 2

Repeating the procedure of Example 1 above, the following compounds, corresponding to the formula:

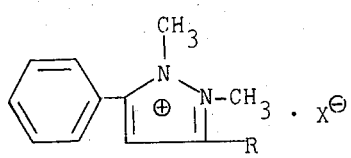

are prepared, and identified in Table I below by substituent R, the anion X and their melting point.

Table 1

| Number | R | X | Melting Point °C |
|---|---|---|---|
| 1 | —NH₂ | I | 176 – 177 |
| 2 | —N(C₃H₇)₂ | ClO₄ | 74 – 75 |
| 3* | —NH—CH(C₂H₅)₂ | I | 189 – 193 |
| 4 | —NH—⟨cyclohexyl⟩ | I | 43 – 46 |
| 5 | —NH—⟨phenyl⟩ | I | 189.5 – 190.5 |
| 6 | —NH—⟨phenyl⟩ | ClO₄ | 171 – 172.5 |
| 7 | —N(CH₃)—⟨phenyl⟩ | ClO₄ | 94 – 96 |
| 8 | —NH—⟨2,6-dimethylphenyl⟩ | I | 199.5 – 202 |

*Acetonitrile used as solvent, instead of ethanol.

EXAMPLE 3

Preparation of 1,2-Dimethyl-5-phenyl-3-(4-pyridyl)pyrazolium Iodide

Sym - dimethylhydrazine dihydrochloride (4.54 g, 0.034 mole), potassium iodide (13 g, 0.078 mole) and absolute ethanol (100 ml) are mixed, stirred and heated at reflux for 3 hours. The mixture is then cooled and filtered. The filtrate is added to a partial solution of the diketone:

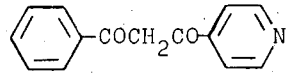

(4.5 g, 0.02 mole) in absolute ethanol (50 ml) and the reaction mixture heated at reflux for 18 hours. The reaction mixture is cooled, the solvent removed in vacuo and the residual oil slurried with a benzene/water mix. The aqueous layer is extracted with chloroform, the chloroform is removed and the residue treated with hexane to yield 1 g of solid, m.p. 166°C to 168°C. The solid is dried, m.p. 171°C to 173°C.

Analysis calculated for: $C_{16}H_{16}N_3I$: C, 50.94; H, 4.28; N, 11.14. Found: C, 50.91; H, 4.52; N, 11.04.

EXAMPLE 4

Preparation of 1,2-Dimethyl-3-dimethylamino-5-phenylpyrazolium Iodide

3-Chloro-1,2-dimethyl-5-phenylpyrazolium iodide (10.0 g, 0.03 mole) is treated with sodium phenoxide (5.64 g, 0.06 mole) in dimethylformamide (100 ml) and the mixture heated and stirred at 110°C to 120°C for 21 hours. The dimethylformamide is then removed in vacuo, the residual oil dissolved in aqueous sodium bicarbonate solution and is extracted with ether. The ether fraction yields some brown oil which is not further examined. Next the aqueous sodium bicarbonate solution is extracted with chloroform (2×150 ml). Evaporation of the chloroform solution yields a white solid which is dried by azeotropic distillation of toluene. Crystallization from a chloroform/ether mixture yields a white solid, m.p. 181.5°C to 182°C.

Analysis calculated for $C_{13}H_{18}N_3I$: C, 45.46; H, 5.28; N, 12.25. Found: C, 45.16; H, 5.23; N, 12.12.

EXAMPLE 5

Preparation of 5-Chloro-1-methyl-3-phenylpyrazole

To a solution of POCl₃ (2,015 g, 19 moles) is added solid 1-methyl-3-phenylpyrazol-2-in-5-one (2,073 g, 11.9 moles) with stirring and warming. At 100°C the mixture becomes homogeneous. The reflux temperature rises from 119°C to 143°C over a period of 30 hours. After cooling, the mixture is poured into ice and water (8 l) with stirring. After 4 hours the slurry is filtered and the filtercake added to 4 l of water containing 1.5 l of 10% sodium hydroxide solution with stirring. Removal of the solid by filtration followed by a recrystallization from hexane gives 1,523 g of product, m.p. 61°C to 62°C.

EXAMPLE 6

Preparation of
1,2-Dimethyl-3-chloro-5-phenylpyrazolium methyl sulfate

Dimethylsulfate (30 g, 0.22 mole) is added to a stirred solution of 1-methyl-5-chloro-3-phenylpyrazole (39.5 g, 0.2 mole) in dry xylene (350 ml) and the reaction mixture is warmed to 105°C to 115°C for 18 hours. A brown syrup separates out, the reaction is cooled and the xylene is decanted off. Dry acetone (300 ml) is added and after stirring a white precipitate separates out and is filtered off, m.p. 100°C to 102°C 33.8 g (55%). Recrystallization from dry acetone-toluene gives white needles m.p. 102°C to 104°C.

EXAMPLE 7

Preparation of
1,2-Dimethyl-3-chloro-5-phenylpyrazolium iodide

To an aqueous solution of 1,2-dimethyl-3-chloro-5-phenylpyrazolium methyl sulfate is added a saturated aqueous solution of sodium iodide at 5°C. A copious precipitate is formed and filtered off. The solid is dissolved in methylene chloride and precipitated with diethyl ether to give almost white crystals, m.p. 162°C to 164°C.

EXAMPLE 8

To determine the effectiveness of pyrazolium salts as foliar fungicidal agents, a variety of pathogenic fungi, host plants and pyrazolium salts are used in the following tests. Pathogens, host plants, the method of testing and the rating system used are reported below along with the data obtained.

Pathogens

*Piricularia oryzae Carvara*, the rice blast pathogen.
*Venturia inaequalis* (Cke.) Wint., which causes apple scab.
*Podosphaera leucotricha* (E.&E.) Salm., the cause of powdery mildew on apples and pears.
*Erysiphe graminis* f. sp. *tritici*, the cause of powdery mildew on wheat.
*Erysiphe graminis* f. sp. *hordei*, the cause of powdery mildew on barley.

Host Plants

Rice (*Oryza sativa* cv. Nato)
Apple (*Malus sylvestris*) (Seedling)
Wheat (*Triticum aestivum* cv. Bonanza)
Barley (*Hordeum vulgare* cv. Larker)

Plants are individually grown in 5.08 cm peat squares and assembled in 7.62 cm × 25.4 cm pressed fibre flats the week prior to spraying. With the exception of rice, barley and wheat, a single specimen of each species is used. A separate container is used for those plants in the mildew evaluation. The complete test system is shown below.

| Series 1 | Series 2 |
| --- | --- |
| Rice: Rice blast | Apple: Powdery Mildew |
| Apple: Apple scab | Wheat: Powdery Mildew |
| | Barley: Powdery Mildew |

Spray solutions are prepared at a final concentration of 500 ppm in 50 ml of 50% aqueous acetone. In all cases acetone is added first to solubilize the compound and solutions made to final volume with deionized water.

Two containers, one from Series 1 and 2 (see above), are sprayed simultaneously on a turntable with 50 ml of the test solution. Spray is provided by 2 fixed Spray System Co. nozzles mounted to deliver vertical and horizontal solid cone patterns. Immediately thereafter, all plants are returned to the greenhouse to permit deposit to dry.

Plants of Series 1 and 2 are separately inoculated. Plants in Series 1 are inoculated with conidial suspensions of the respective pathogens using a De Vilbiss paint sprayer operated at 0.28 to 0.42 kg/cm² pressure and is transferred to a controlled temperature/humidity cabinet (ambient temperature, RH ~ 95 percent). Plants in Series 2 are dusted with respective powdery mildew conidia and then removed to the greenhouse, to await disease development. All plants are rated for disease severity on a scale of 1–7 (clean – kill), as described below:

| Rating | Description |
| --- | --- |
| 1 | Nil |
| 2 | Trace disease |
| 3 | Slight disease |
| 4 | Moderate disease |
| 5 | Heavy disease |
| 6 | Severe disease |
| 7 | Kill |

In the accompanying Tables of results, the numerical rating is used for clarity. Also given is a rating for the controls or checks. Data are reported for the minimum effective level at which the compounds were tested. Where more than one test has been conducted, the ratings are average and reported as a single value rating.

Table II

Disease severity of Plants Sprayed to Run-off with Indicated Minimum Effective Rate (ppm)
(Series 1)

| Compound | Rice Blast 500 | Apple Scab 500 |
| --- | --- | --- |
| Untreated Controls Average Rating | 5.1 | 5.4 |
| 3-Amino-1,2-dimethyl-5-phenylpyrazolium iodide | 4.7 | 4.0 |
| 1,2-Dimethyl-3-dimethylamino-5-phenyl-pyrazolium iodide | 4.7 | |
| 1,2-Dimethyl-3-phenyl-5(4-pyridyl)-pyrazolium iodide | 4.0 | |

Table II-continued

Disease severity of Plants Sprayed to Run-off with Indicated Minimum Effective Rate (ppm) (Series I)

| Compound | Rice Blast 500 | Apple Scab 500 |
|---|---|---|
| 1,2-Dimethyl-3-(4-methyl-1-piperazinyl)-5-phenylpyrazolium iodide | 4.0 | |

Table III

Disease Severity of Plants Sprayed to Run-off with Indicated Minimum Effective Rate (ppm) (Series II)

| Compound | Wheat Powdery 500 | Apple Powdery 500 | Barley Powdery 500 |
|---|---|---|---|
| Untreated Controls Average Rating | 5.9 | 5.6 | 5.4 |
| 3-Amino-1,2-dimethyl-5-phenyl-pyrazolium iodide | 3.3 | 4.7 | 4.5 |
| 1,2-Dimethyl-3-dimethylamino-5-phenylpyrazolium iodide | 3.8 | | 4.0 |
| 3-Cyclohexylamino-1,2-dimethyl-5-phenylpyrazolium iodide | 1.0 | | 1.0 |
| 1,2-Dimethyl-3-phenyl-5-(4-pyridyl)pyrazolium iodide | 4.0 | 4.0 | — |
| 1,2-Dimethyl-3-(4-methyl-1-piperazinyl)-5-phenylpyrazolium iodide | | 4.0 | — |

I claim:

1. A method for the control of plant pathogenic fungi which comprises the step of: contacting said pathogenic fungi with a fungicidally effective amount of a compound having the formula:

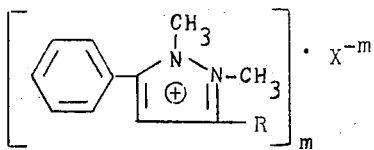

where R is 4-pyridyl or a member represented by the formula:

$-NR_1R_2$ and wherein $R_1$ and $R_2$ are each a member selected from the group consisting of hydrogen, alkyl $C_1-C_6$, cycloalkyl $C_3-C_6$, benzyl, phenyl, 2,3-xylyl or radical:

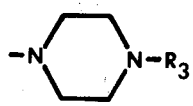

where $R_3$ is hydrogen or methyl; X is an anion having a charge of from 1 to 3 and is selected from the group consisting of chloride, bromide, iodide, acetate, sulfate, hydrogen sulfate, methyl sulfate, benzene sulfonate, p-toluene sulfonate, nitrate, phosphate, carbonate and perchlorate, tetrafluoroborate; and $m$ is an integer selected from 1 to 3.

2. The method according to claim 1, for the control of plant pathogenic fungi wherein said plant pathogenic fungi is contacted with from 1 ppm to 5,000 ppm of said active compound.

3. The method according to claim 1 wherein the compound is 3-amino-1,2-dimethyl-5-phenyl-pyrazolium iodide.

4. The method according to claim 1, wherein the compound is 1,2-dimethyl-3-dimethylamino-5-phenyl-pyrazolium iodide.

5. The method according to claim 1 wherein the compound is 1,2-dimethyl-5-phenyl-3-dipropylaminopyrazolium perchlorate.

6. The method according to claim 1, wherein the compound is 1,2-dimethyl-3(3-pentylamino)-5-phenyl-pyrazolium iodide.

* * * * *